(12) United States Patent
Takenawa et al.

(10) Patent No.: US 6,472,193 B1
(45) Date of Patent: Oct. 29, 2002

(54) RECOMBINANT LYSOPHOSPHATIDIC ACID PHOSPHATASE

(75) Inventors: Tadaomi Takenawa, Tokyo; Masami Hiroyama, Kawasaki; Tatsuya Kishimoto, Suita; Masahiro Yamaguchi, Ibaraki; Mitsuyoshi Toyosato; Kouji Mizuno, both of Kyoto, all of (JP)

(73) Assignee: Azwell Inc., Osaka (JP)

( * ) Notice: Subject to any disclaimer, the term of this patent is extended or adjusted under 35 U.S.C. 154(b) by 0 days.

(21) Appl. No.: 09/600,588

(22) PCT Filed: Aug. 23, 1999

(86) PCT No.: PCT/JP99/04509
§ 371 (c)(1),
(2), (4) Date: Sep. 11, 2000

(87) PCT Pub. No.: WO00/31275
PCT Pub. Date: Jun. 2, 2000

(30) Foreign Application Priority Data

Nov. 19, 1998 (JP) .............................. 10-329866

(51) Int. Cl.[7] .......................... C12N 9/14; C12N 9/16; C12Q 1/42; C07H 21/04
(52) U.S. Cl. ................... 435/196; 435/195; 435/21; 536/23.2
(58) Field of Search .................. 536/23.2; 435/21, 435/195, 196

(56) References Cited

FOREIGN PATENT DOCUMENTS

WO  9914328  3/1999

OTHER PUBLICATIONS

Broun et al., Science 282:1315–1317, 1998.*
Van de Loo et al., Proc. Natl. Acad. Sci. 92:6743–6747, 1995.*
Smith et al., Nature Biotechnology 15:1222–1223, 1997.*
Xie et al., Arch. Biochem. Biophys., 1994, 312:254–259.*
Thompson et al., Biochem, J., vol. 300, No. 2, pp. 457–461 (1994).
Waggoner et al., Journal of Biological Chemistry, vol. 270, No. 33, pp. 19422–19429 (1995).
Waggoner et al., Journal of Biological Chemistry, vol. 271, No. 28, pp. 16506–16509 (1996).
Hiroyama et al., Biochem. J., vol. 336, pp. 483–489 (1998).
Hiroyama et al., Journal of Biological Chemistry, vol. 274, No. 41, pp. 29172–29180 (1999).

* cited by examiner

Primary Examiner—Ponnathapu Achutamurthy
Assistant Examiner—Delia Ramirez
(74) Attorney, Agent, or Firm—Birch, Stewart, Kolasch & Birch, LLP

(57) ABSTRACT

An object of the present invention is to provide a recombinant LPA phosphates capable of specifically hydrolyzing LPA, which is useful for elucidation of the metabolic pathway of LPA, and also for diagnosis and treatment of various diseases with which LPA is associated. The present invention also provides for a method capable of simply and inexpensively determining LPA associated with various diseases. The present invention also provides for a kit for determination suitable for the method. The present invention has succeeded in purifying the LPA phosphatase using bovine brain as a raw material, and further in cloning human LPA phosphatase gene. The present invention specifically relates to a DNA encoding a peptide comprising the amino acid sequence of SEQ ID NO:1; a DNA comprising the nucleotide sequence of SEQ ID NO:2; a protein encoded by the DNA; and expression vector carrying the DNA; a transformant harboring the expression vector; a method for producing a recombinant lysophosphatidic acid phosphatase by the transformant; a method for determination of LPA by the protein; a determination reagent for LPA by the protein; a kit for diagnosis, comprising the reagent for determination, and the like.

7 Claims, 11 Drawing Sheets

RECOMBINANT LYSOPHOSPHATIDIC ACID PHOSPHATASE

This application is the national phase under 35 U.S.C. §371 of PCT International Application No. PCT/JP99/04509 which has an International filing date of Aug. 23, 1999, which designated the United States of America.

TECHNICAL FIELD

The present invention relates to a recombinant lysophosphatidic acid phosphatase (LPA phosphatase). More particularly, the present invention relates to a DNA encoding an LPA phosphatase, a protein encoded by the DNA, an expression vector carrying the DNA, a transformant harboring the expression vector, a process for preparing the protein, an antibody against the protein, an antisense DNA or RNA complementary to the DNA, an oligonucleotide probe or primer capable of specifically hybridizing to the DNA, a method for determination of LPA using a recombinant LPA phosphatase, a determination reagent and a kit for diagnosis.

BACKGROUND ART

Lysophosphatidic acid (LPA) is a naturally-occurring phospholipid having the simplest chemical structure, and it has been known to exhibit a growth factor-like activity against the fibroblasts [Moolenaar, W. H. et al., (1992) *Rev. Physiol. Biochem. Pharmacol.* 119, 47–65; Moolenaar, W. H., (1995) *J. Biol. Chem.* 270, 12949–12952; Moolenaar, W. H. et al., (1997) *Curr. Opinion Cell Biol.* 9, 168–173]. The LPA is rapidly produced and released as a product of the coagulation process of blood from the activated platelets. Therefore, it is suggested that the LPA has a kind of a role in healing of a wound and regeneration. Also, there is clarified that the LPA induces rapid retraction of the axon and transient formation of spheres of cell bodies in neurocytes. These biological activities are thought to be caused by LPA receptor conjugated with G protein [Moolenaar, W. H. et al., (1997) *Curr. Opinion Cell Biol.* 9, 168–173], and a cDNA encoding two deduced LPA receptors has been isolated [Hecht, J. H. et al. (1996) *J. Cell Biol.* 135, 1071–1083; Guo, Z. et al. (1996) *Proc. Natl. Acad. Sci. USA* 93: 14367–14372].

In addition, the LPA possesses various biological activities such as promotion of cancer cell invasion, cell adhesion, suppression of apoptosis, and chemotaxis. Moreover, there has been reported that its amount present in sera is high in ovarian cancer and other gynecologic malignancies [Xu, Y. et al. (1998) *JAMA* 280, 719–723], and it is expected to also serve as a marker for early detection of cancers.

Regarding the production of the LPA, there has been known that the LPA is synthesized by generation from monoacylglycerol by monoacylglycerol kinase, generation from phosphatidic acid by phospholipase A1 (PLA1) or phospholipase A2 (PLA2), and the like. However, since the LPAs produced in response to various stimuli take place at a slightly delayed stage as compared to the generation of phosphatidic acid (PA) [Gait, F. et al. (1997) *FEBS Lett.* 410, 54–58], it is thought that those ascribed to the latter pathway are dominant.

However, the LPA in the biosynthesis system is immediately converted to phosphatidic acid, so that it is thought that most of the cases where the LPA acts as a bioactive substance is not made from the synthesis system but as a product of a phospholipid degradation system. Regarding the hydrolytic pathways of the LPA, there are possibly three pathways, namely pathways with LPA phospholipase A, LPA phosphatase and LPA acyltransferase [Gait, F. et al., (1997) *FEBS Lett.* 410, 54–58; Eberhardt, C. et al., (1997) *J. Biol. Chem.* 272, 20299–20305]. Since the LPA is a bioactive lipid, it is thought that the exclusion of the LPA by the above enzyme plays an extremely important role in termination of the signal.

Regarding LPA phospholipase A, one purified from rat brain has been known, which is a membrane bound enzyme of a size of 80 kDa, and hydrolyzes LPA but does not hydrolyze other lysophospholipids [Thompson, F. J. and Clark M. A., (1994) *Biochem. J.* 300, 457–461].

Regarding the LPA phosphatase, there has been reported the presence of ecto-(lyso)phosphatidic acid phosphatase that also hydrolyzes PA in PAM212 mouse keratinocytes [Xie, M. and Low, M. G., (1994) *Archives Biochemistry Biophysics* 312, 254–259]. Until recently, a membrane bound PA phosphatase which is relatively PA-specific but also exhibits a weak activity for LPA has been purified from porcine thymus [Kanoh, H. et al., (1992) *J. Biol. Chem.* 267, 25309–25314; Kai, M. et al., (1996) *J. Biol. Chem.* 271, 18931–18938]. In addition, a membrane bound PA phosphatase, which also hydrolyzes LPA, ceramide 1-phosphate and sphingosine 1-phosphate, is purified from rat liver [Waggoner, D. W. et al., (1995) *J. Biol. Chem.* 270, 19422–19429; Waggoner, D. W. et al., (1996) *J. Biol. Chem.* 271, 16506–16509]. However, there has not yet been known LPA-specific phosphatase at present.

Further, regarding the method for determination of LPA, there has been known a method comprising extracting lipid components from a sample, separating LPA from other lipid components by thin layer chromatography, and thereafter determining the resulting LPA by gas chromatography as a methyl ester of a fatty acid via transmethylation reaction [Xu, Y. et al. (1998) *JAMA* 280, 719–723]. However, this method requires complicated procedures, so that it has a defect that a length of time period is required for assay of a large number of samples.

DISCLOSURE OF INVENTION

The present invention has been accomplished in view of the above prior art, and an object of the present invention is to provide a recombinant LPA phosphatase capable of specifically hydrolyzing LPA, which is useful for elucidation of the metabolic pathway for LPA, and also for diagnosis and treatment for various diseases with which LPA is associated; a method capable of simply and inexpensively determining LPA associated with various diseases; a determination reagent suitable for the method; a kit suitable for diagnosis of a disease with which LPA is associated, and the like.

The present inventors have confirmed the presence of the LPA phosphatase activity in bovine brain, and purified the LPA phosphatase using bovine brain as a raw material, and further proceeded with the study. As a result, they have succeeded in cloning human LPA phosphatase gene, and the present invention has been perfected thereby.

The gist of the present invention relates to:

[1] a DNA encoding a lysophosphatidic acid phosphatase, wherein the DNA is selected from the group consisting of:
  (a) a DNA encoding a peptide comprising the amino acid sequence of SEQ ID NO: 1;
  (b) a DNA encoding a peptide comprising an amino acid sequence resulting from deletion, substitution, insertion or addition of one or more amino acids in the amino acid sequence of SEQ ID NO: 1;

(c) a DNA comprising the nucleotide sequence of SEQ ID NO: 2;

(d) a DNA comprising a nucleotide sequence resulting from deletion, substitution, insertion or addition of one or more bases in the nucleotide sequence of SEQ ID NO: 2;

(e) a DNA capable of hybridizing to the DNA of any one of the above (a) to (d), under stringent conditions;

[2] a protein encoded by the DNA of item [1] above;

[3] an expression vector carrying the DNA of item [1] above;

[4] a transformant harboring the expression vector of item [3] above;

[5] a method for producing a recombinant lysophosphatidic acid phosphatase, comprising the step of culturing the transformant of item [4] above under conditions capable of expressing a protein from the expression vector of item [3] above;

[6] an antibody or a fragment thereof, capable of specifically binding to the protein of item [2] above;

[7] an antisense DNA or antisense RNA comprising 8 bases or more, having a sequence complementary to the DNA of item [1] above;

[8] a probe or primer, capable of specifically hybridizing to the DNA of item [1] above;

[9] a method for determination of LPA, comprising the step of mixing the protein of item [2] above with a sample to be tested;

[10] the method for determination of LPA according to item [9] above, wherein the presence or absence of a product resulting from hydrolysation of lysophosphatidic acid by the protein of item [2] above is used as an index of the presence or absence of lysophosphatidic acid;

[11] the method for determination of LPA according to item [10] above, wherein phosphoric acid or monoacyl glycerol is determined as the hydrolysate of lysophosphatidic acid;

[12] a determination reagent for LPA, comprising the protein of item [2] above;

[13] the determination reagent for LPA according to item [12], further comprising a reagent for determining phosphoric acid or monoacyl glycerol; and

[14] a kit for diagnosing a disease in which LPA is involved, comprising the determination reagent for LPA of item [12] or [13] above.

BEST MODE FOR CARRYING OUT THE INVENTION

Figure 1:
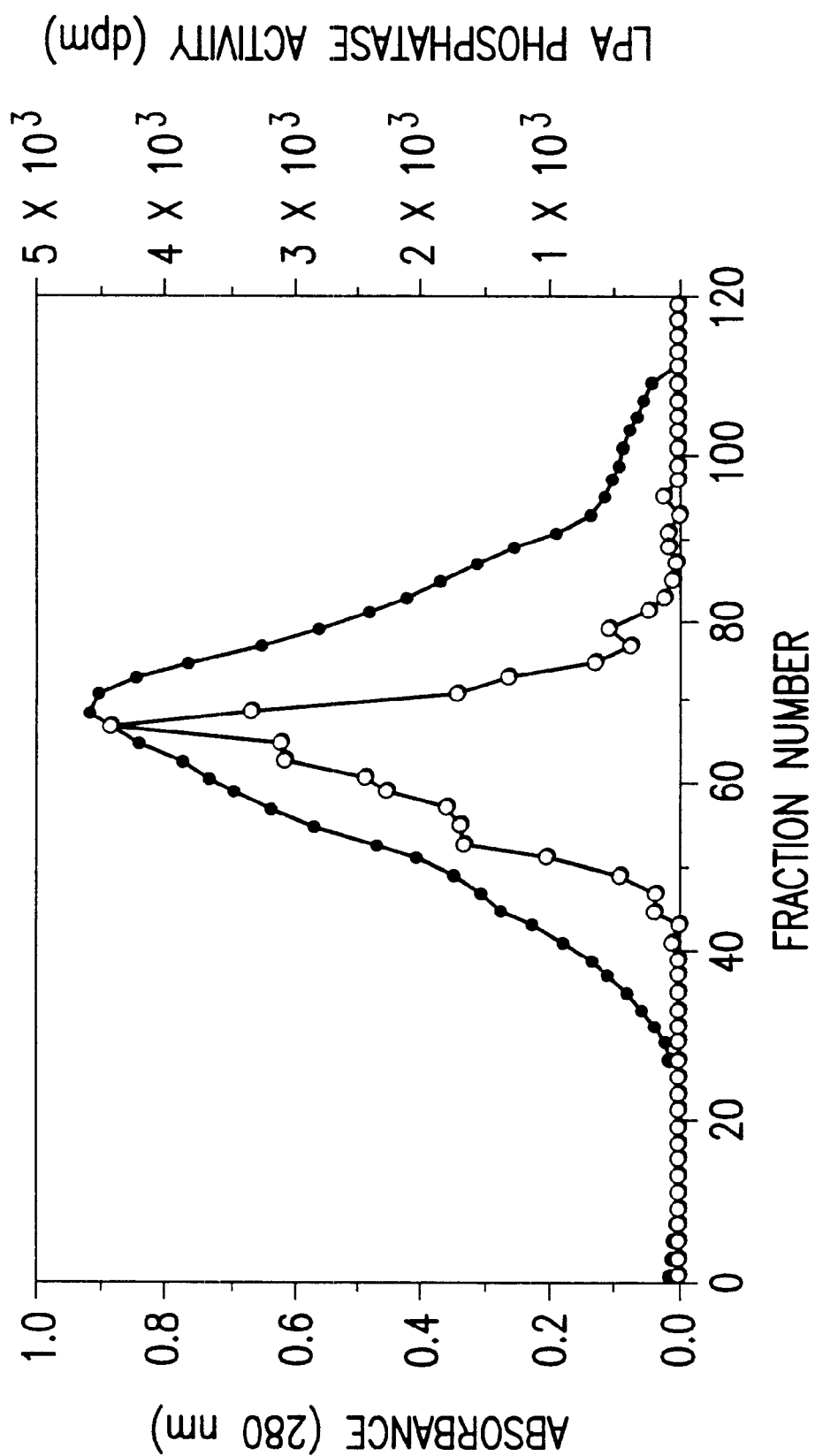
FIG. 1 is a graph showing the results of ion exchange chromatography by Q Sepharose FF.

The lysophosphatidic acid phosphatase (LPA phosphatase) of the present invention is a protein encoded by the DNA of the present invention described below, the protein possessing an activity capable of specifically hydrolyzing phosphate ester of lysophosphatidic acid (hereinafter abbreviated as "LPA phosphatase activity" in some cases). Concretely, there is included a peptide comprising the amino acid sequence of SEQ ID NO: 1. This peptide is a protein having 421 amino acid residues, and is human LPA phosphatase.

Regarding the substrate specificity of the LPA phosphatase of the present invention, it has features of specifically hydrolyzing lysophosphatidic acid, but not hydrolyzing phosphatidic acid, cardiolipin, bisphosphatidic acid, glycerophosphate, ceramide 1-phosphate, and sphingosine 1-phosphate.

In the present invention, the substrate LPA includes 1-oleoyl-lysophosphatidic acid (1-oleoyl-LPA), 1-palmitoyl-LPA, 1-stearoyl-LPA, 1-myristoyl-LPA, 1-lauroyl-LPA, 1-linoleoyl-LPA, and the like. In the present specification, when simply identified as "LPA," the technical idea encompasses the above-mentioned 1-oleoyl-LPA, 1-palmitoyl-LPA, 1-stearoyl-LPA, 1-myristoyl-LPA, 1-lauroyl-LPA, 1-linoleoyl-LPA, and the like.

The activity of the LPA phosphatase of the present invention can be assayed by a usual method. For instance, the activity may be assayed by the following method.

A reaction is carried out is reacted at 37° C. for 15 minutes in 50 mM Tris-maleate buffer (50 µl) at a pH of 7.5 containing 50 µM [³H]1-oleoyl-LPA (5×10⁴ dpm), a detergent, and an enzyme. Two-hundred and fifty microliters of Dole reagent (isopropanol/heptane/1 N H₂SO₄=78/28/2) is added thereto to terminate the reaction, and subsequently 125 µl of H₂O and 150 µl of heptane are added to the resulting reaction product. After mixing, the resulting mixture is centrifuged (1200×g, 5 minutes). One-hundred and fifty microliters of the upper layer is taken into another tube, and thereafter 150 μl of heptane and a microspatula amount of silica gel 60H are added and mixed. The mixture is centrifuged (1,200 g, 5 minutes), and 200 μl of the supernatant is added to 2 ml of Scintisol EX-H. The generated [$^3$H]-monooleoyl-glycerol is measured by a scintillation counter to determine an enzyme activity.

The DNA of the present invention is a DNA encoding an LPA phosphatase, which is selected from the group consisting of:

(a) a DNA encoding a peptide comprising the amino acid sequence of SEQ ID NO: 1;

(b) a DNA encoding a peptide comprising an amino acid sequence resulting from deletion, substitution, insertion or addition of one or more amino acids in the amino acid sequence of SEQ ID NO: 1;

(c) a DNA comprising the nucleotide sequence of SEQ ID NO: 2;

(d) a DNA comprising a nucleotide sequence resulting from deletion, substitution, insertion or addition of one or more bases in the nucleotide sequence of SEQ ID NO: 2; and (e) a DNA capable of hybridizing with a DNA of any one of the above items (a) to (d) mentioned above, under stringent conditions.

The DNA of the present invention is concretely a DNA encoding a peptide comprising the amino acid sequence of SEQ ID NO: 1, and more concretely a DNA comprising the nucleotide sequence of SEQ ID NO: 2, which is human LPA phosphatase gene.

The DNA of the present invention also encompasses a DNA encoding a peptide comprising an amino acid sequence resulting from deletion, substitution, insertion or addition of one or more amino adds in the amino acid sequence of SEQ ID NO: 1, as long as the peptide possesses an LPA phosphatase activity. The term "one or more" in the present specification means a number of one or several or more.

In addition, the DNA of the present invention also encompasses a DNA comprising a nucleotide sequence resulting from deletion, substitution, insertion or addition of one or more bases in the nucleotide sequence of SEQ ID NO: 2, as long as the peptide encoded by the DNA possesses an LPA phosphatase activity. Here, the term "one or more" has the same meaning as described above.

In the present specification, "deletion, substitution, insertion or addition of amino acids and bases" may be those which are naturally occurring or those which are artificially introduced. The procedures for deletion, substitution, insertion or addition of amino acids and bases mentioned above can be readily performed by one of ordinary skill in the art by site-directed mutagenesis, PCR method, or the like as described in, for instance, Sambrook, J. et al., *Molecular Cloning: A Laboratory Manual*, 2nd edition, Cold Spring Harbor Laboratory Press, New York, published in 1989.

Further, the DNA of the present invention also encompasses a DNA capable of hybridizing with a DNA of any one of (a) to (d) mentioned above, under stringent conditions, as long as the peptide encoded by the DNA has an LPA phosphatase activity.

In the present specification, the term "capable of hybridizing under stringent conditions" refers to a state in which positive hybridization signals are still observed even under the conditions, for instance, of heating at 42° C. in a solution containing 6×SSC (20×SSC refers to 333 mM sodium citrate and 333 mM NaCl), 0.5% SDS and 50% formamide, and thereafter washing at 68° C. in a solution containing 0.1× SSC and 0.5% SDS.

The DNA of the present invention is obtained as follows. Concretely, bovine brain is homogenized in an appropriate buffer, and the resulting homogenate is centrifuged, to give a cytosol fraction. Next, this fraction is fractionated with ammonium sulfate by a conventional method, and thereafter ion exchange chromatography, gel filtration, adsorption chromatography and the like are employed in combination, whereby purified LPA phosphatase can be obtained. A partial amino acid sequence of the bovine LPA phosphatase obtained in the manner described above is determined, and a synthetic oligonucleotide primer is prepared on the basis of the determined amino acid sequence. PCR method is carried out using DNA of gene library as a template, to give cDNA fragment. LPA phosphatase cDNAs derived from various organisms and tissues can be obtained by screening various gene libraries using the resulting cDNA fragment as a probe.

The expression vector of the present invention carries the DNA mentioned above. The expression vector usable in the present invention includes, for instance, commercially available expression vectors or known expression vectors, such as pUC derivatives, pGEX-2T, pQE30, pET, pKK223-3, pMSG, and PSVL, and the expression vector is not particularly limited, as long as the expression vector is a vector capable of inserting the DNA of the present invention thereinto, and expressing the DNA.

As a method for inserting the DNA of the present invention into a vector, there can be performed a method as described in *Molecular Cloning*, mentioned above, and the like.

The transformant of the present invention is those obtained by introducing the above expression vector into a desired host cell. The host cells may be any of prokaryotic cells such as *Escherichia coli* [HB101, JM109, and the like], and bacteria of the genus Bacillus [*Bacillus subtilis* and the like]; or eukaryotic cells such as yeasts of the genus Saccharomyces [*Saccharomyces cerevisiae* and the like], insect cells [*Spodoptera frugiperda* cells such as Sf9, *Bombyx mori* cells and the like], mammalian cells [monkey cells such as COS1 and COS7, murine cells such as NIH3T3, and human cells such as HeLa cells], which is selected depending upon the expression vector used.

As a method for introducing an expression vector, a known method, including, for instance, calcium phosphate method, lipofection method, DEAE dextran method, electroporation method [edited by Ausubel, F. M. et al., *Current Protocols in Molecular Biology*, John Wiley & Sons, Inc. (1987)], or the like may be employed.

The present invention provides a method for producing a recombinant LPA phosphatase comprising the step of culturing under conditions capable of expressing the protein of the present invention from the above expression vector. The case where *E. coli* is selected as a host cell and pGEX-2T is used as an expression vector is described as follows.

In order to express the LPA phosphatase as a fusion protein with GST (glutathione-S-transferase) in *E. coli*, GST-LPA phosphatase expression plasmid is prepared by inserting cDNA of the LPA phosphatase to an expression plasmid pGEX-2T. Next, *E. coli* is transformed with the expression plasmid, and the resulting transformant is cultured under usual conditions. Subsequently, isopropyl-β-D-thiogalactoside (IPTG) is added to the resulting transformant in the logarithmic growth phase, to continue culturing, thereby inducing expression of GST-LPA phosphatase fusion protein. The expressed fusion protein can be purified with glutathione beads.

In addition, the recombinant LPA phosphatase, which is not a fusion protein, can be purified by such a method as usual ultrafiltration method, column chromatography, or affinity purification using the antibody of the present invention.

Further, the present invention provides an antibody or a fragment thereof, capable of specifically binding to the protein of the present invention. The antibody may be a polyclonal antibody or monoclonal antibody.

The antibody of the present invention can be readily prepared by appropriately immunizing an animal using all or a part of the protein of the present invention in accordance with the method described in, for instance, *Antibodies: A Laboratory Manual*, edited by Lane, H. D. et al., published by Cold Spring Harbor Laboratory Press, New York, 1989, or the like, thereby readily giving an antibody capable of specifically binding to the protein of the present invention or an antibody neutralizing its activity. In addition, an antibody fragment can be prepared by cleaving the resulting antibody with a protease, or the like.

The application of the antibody or fragment thereof includes affinity chromatography, screening of cDNA library, immunological diagnostic method, pharmaceuticals, and the like. The immunological diagnostic method can be appropriately selected from immunoblotting method, radio-immunoassay (RIA), enzyme immunoassay (ELISA), fluorescence or luminescence assay, or the like.

The present invention provides an antisense DNA or antisense RNA comprising 8 bases or more, and having a sequence complementary to the DNA of the present invention. The antisense DNA or antisense RNA can be obtained by artificial synthesis using a synthesizer, by transcription of a DNA in an opposite direction to the usual direction (namely antisense direction), or the like.

The above antisense DNA or antisense RNA can be introduced into a cell, whereby the expression of the protein of the present invention can be suppressed. In view of the above, the length of the antisense DNA or antisense RNA is usually 8 to 1700 bases, preferably 15 to 30 bases. While mRNA produced by usual transcription of a gene is a sense strand, the antisense DNA or antisense RNA binds to the sense strand mRNA intracellularly, so that the translation from the mRNA is suppressed, thereby controlling the production of the LPA phosphatase, the protein of the present invention. By having the above action, the antisense DNA or antisense RNA is used, for instance, as a regulating agent for LPA phosphatase activity. In addition, the antisense DNA or antisense RNA can be utilized as a research reagent for in situ hybridization, or the like.

Whether or not the prepared antisense DNA or antisense RNA has the desired suppressive effects can be readily found from, for instance, the following two methods. One is a method of directly introducing from outside of the cells an antisense DNA or antisense RNA into the cells expressing the LPA phosphatase of the present invention, and thereafter evaluating a change in the expression level of the LPA phosphatase as an index; and the other is a method of introducing a vector capable of producing the antisense RNA by transcription into the above LPA phosphatase expressing cells, and thereafter evaluating a change in the expression level of the LPA phosphatase as an index.

The present invention provides a probe or primer, capable of specifically hybridizing to the DNA of the present invention. The length of the probe or primer can be selected in accordance with its purpose. The length of the probe is usually 8 to 1700 bases, preferably 13 to 1300 bases, and the length of the primer is usually 8 to 50 bases, preferably 15 to 35 bases. The probe or primer can be usually prepared by chemical synthesis using a synthesizer, or enzymatic synthesis using DNA polymerase I (Klenow fragment), or PCR method.

The hybridization conditions for the probe or primer of the present invention can be easily set depending upon the purposes in accordance with the method as described in, for instance, Sambrook, J. et al., *Molecular Cloning: A Laboratory Manual*, 2nd edition, Cold Spring Harbor Laboratory Press, New York, published in 1989.

The probe or primer of the present invention is expected to be used for detection and quantitation of the LPA phosphatase, to play a role in diagnosis or treatment in the diseases associated with the LPA phosphatase. In addition, the probe or primer can be also utilized as a research reagent for the LPA phosphatase used in hybridization, PCR, or the like.

The LPA phosphatase of the present invention, as described above, is an enzyme which is capable of specifically acting to LPA, to remove phosphate group, thereby forming monoacylglycerol. Besides having the action of promoting cell proliferation, the LPA possesses various biological activities such as promotion of cancer cell invasion, cell adhesion, suppression of apoptosis, agglutination of platelets, and chemotaxis, and there have been reports suggesting its relationship with the diseases. Therefore, it can be applied to diagnosis of a disease associated with the LPA by determining LPA using the LPA phosphatase of the present invention. The present invention provides a method for determination of such an LPA.

Here, the diseases associated with LPA or LPA phosphatase are not particularly limited, and include, for instance, cancer such as ovarian cancer, peritoneal cancer, endometrial cancer or endocervical cancer.

The method for determination of LPA of the present invention comprises the step of mixing the LPA phosphatase, which is the protein of the present invention, with a sample to be tested. In the method for determination, the presence or absence of a hydrolysate of LPA is used as an index of the presence or absence of the lysophosphatidic acid.

The sample to be tested includes body fluids and tissues such as blood, plasma, sera, and urine. When the sample to be tested is a collected tissue, the LPA can be determined by appropriately carrying out pretreatments such as tissue homogenizing treatment, and cell lysis treatment.

The conditions for mixing the LPA phosphatase with the sample to be tested may be conditions capable of exhibiting the activity of the LPA phosphatase, including, for instance, reactive pH ranges and temperatures. In addition, as described below, when carried out by a coupling reaction of the reaction of the LPA phosphatase with the reaction for determination of hydrolysate, the coupling reaction can be carried out under conditions that both reactions can be performed.

When LPA is contained in the sample to be tested, in the step of mixing the protein of the present invention with the sample to be tested, the LPA phosphatase, which is the protein of the present invention, is reacted with the LPA in the sample to be tested, thereby forming a hydrolysate of the LPA.

The hydrolysates of LPA are monoacylglycerol and phosphate.

In the method for determination of LPA of the present invention, since the LPA phosphatase, which is the protein of the present invention, is used, the method can be carried out remarkably simply and inexpensively, as compared with the conventional method for determination of LPA.

Next, the formed hydrolysate (monoacylglycerol or phosphate) is determined. As the method for determination of monoacylglycerol or phosphate, a known method can be employed therefor, respectively. The reaction for detecting monoacylglycerol or phosphate may be simultaneously carried out with the reaction of the LPA phosphatase.

The method for determination of monoacylglycerol includes, for instance, a method for quantifying hydrogen peroxide generated by acting monoacylglycerol with monoacylglycerol lipase and glycerol oxidase, or by acting monoacylglycerol with monoacylglycerol lipase, glycerol kinase and glycerol-3-phosphate oxidase (Japanese Patent Laid-Open No. Sho 63-245672 and the like). In addition, using glycerol-3-phosphate dehydrogenase in place of glycerol-3-phosphate oxidase in the above method, an amount of changes in the reduced nicotinamide adenine dinucleotide (NADH) or reduced nicotinamide adenine dinucleotide phosphate (NADPH), generated from oxidized nicotinamide adenine dinucleotide ($NAD^+$) or oxidized nicotinamide adenine dinucleotide phosphate ($NADP^+$) is as an index. Alternatively, the amount of changes in the oxidized form may be used as an index.

The method for determination of phosphate includes, for instance, chemical methods such as phosphomolybdate reduction method and phosphomolybdate direct method; and enzymatic method which can be carried out under more specific and simpler conditions. In the present invention, from the viewpoint of being capable of performing under more specific and simpler conditions, the enzymatic phosphate determination method is desirable. Alternatively, the sample to be tested may be pre-treated with the LPA phosphatase, and thereafter free phosphate is determined by the chemical method mentioned above.

The enzymatic phosphate determination method includes a method for determining hydrogen peroxide generated by reacting phosphoric acid with inosine in the presence of purine nucleoside phosphorylase, to generate hypoxanthine, and further allowing to act the generated hypoxanthine with xanthine oxidase (Adam A. et al., (1984) *Clin. Chem.* 30, 1724); a method for determining NADH generated by reacting hypoxanthine with $NAD^+$ using xanthine dehydrogenase in place of xanthine oxidase in the above method; a method for determining hydrogen peroxide generated by reacting phosphoric acid with pyruvic acid in the presence of pyruvate oxidase; a method for quantifying NADH generated by reacting phosphoric acid with glycogen in the presence of sucrose phosphorylase, thereafter allowing to act the generated glucose-1-phosphate with phosphoglucomutase, and acting the generated $NAD^+$ with glucose-6-phosphate dehydrogenase [Ryo Fushimi, (1987) *Kensa to Gijutsu* 15, 137–140]. Even when utilizing such enzymatic determination methods, the sample may be pre-treated with the LPA phosphatase, and thereafter free phosphate is determined by enzymatic method. Alternatively, the method may be performed by simultaneously carrying out a coupling reaction of an LPA phosphatase reaction with a reaction for determination of a phosphate.

In the above enzymatic method for determination of monoacylglycerol or phosphate, when hydrogen peroxide is generated by an enzymatic reaction, the hydrogen peroxide can be determined by such methods as a method using hydrogen peroxide electrodes, a colorimetric quantitation method using peroxidase (POD), catalase, or the like. When the POD is used, there is widely used a method for determining a dye generated by oxidation condensation reaction of 4-aminoantipyrine with a color coupler, and the determination can be made at high sensitivity by using fluorescence reaction and luminescence reaction.

In addition, in the above enzymatic method for determination of monoacylglycerol or phosphate mentioned above, when NADH or NADPH is generated, the NADH or NADPH can be determined by utilizing the changes in absorbance.

The determination reagent for the LPA of the present invention comprises the LPA phosphatase, which is the protein of the present invention. The reagent may further comprise a substance associated with the determination of monoacylglycerol or phosphate, which is a hydrolysate of the LPA.

In the determination reagent for the LPA of the present invention, the LPA phosphatase may be subjected to appropriate to chemical modifications for the purpose of stabaliization, or it may be used as an immobilized enzyme prepared by immobilizing an enzyme to an appropriate carrier.

The above determination reagent is usually provided as a reagent kit for determination comprising a reagent prescribed so that each substance including the enzyme has an appropriate concentration. The reagent form in this case may be dry powder or liquid without particular limitation, and an activator, a stabilizer for an enzyme, an antiseptic, or the like may be also added. In addition, the reagent kit may be a kit which comprises two or more kinds of reagents with different timing for addition to the reaction mixture, as in the case of a combination of a reagent for a first reaction and a reagent for a second reagent, and it may be a single reagent system.

The kit for diagnosis of the present invention is useful in diagnosis for a disease associated with the LPA, which comprises the determination reagent mentioned above. The above kit may further comprise a reagent for collecting a sample to be tested, a reagent for treating the sample to be tested, and a control sample for diagnosing.

The pharmaceutical comprising the LPA phosphatase of the present invention as an active ingredient complements intrinsic LPA phosphatase activity for an individual suffering from a disease associated with LPA or LPA phosphatase, whereby the lysophosphatidic acid phosphatase can be supplied in an amount sufficient for degrading the LPA at a level causative of such diseases.

The LPA phosphatase contained in the above pharmaceutical can be present as a protein, or can be present in the form of an expression vector so as to exhibit an activity by expression of the LPA phosphatase in the bodies of individuals.

When the above pharmaceutical is used to an individual who is suspected to have a cancer which is thought to be associated with LPA or LPA phosphatase, or to an individual who suffers from such a disease, the cancer can be treated, and further the metastasis of cancers can be prevented.

The present invention will be explained in further detail by means of the working examples, without intending to limit to these examples.

Preparation Example 1

Purification of Bovine LPA Phosphatase

All of the following steps were carried out at 0° to 4° C.
(1) Homogenization Step Buffer [20 mM Tris-HCl (pH 7.5), 1 mM EDTA, 0.1 mM phenylmethyl sulfonyl fluoride, 1 mg/ml aprotinin, 1 mg/ml leupeptin] was added to bovine brain (1600 g), so as to have a concentration of 1.5 ml/g, and the mixture was homogenized by National mixer MX-V100. The homogenate was centrifuged at 12,000×g for 30 minutes, and the resulting supernatant was further centrifuged at 100,000×g for 1 hour, to give a supernatant cytosol fraction (9,600 mg as an amount of protein).

(2) Ammonium Sulfate Fractionation

Ammonium sulfate was added to the above cytosol fraction so as to give a 35% saturated solution, and the mixture was stirred at 4° C. for 1 hour, and thereafter centrifuged (12,000×g for 30 minutes). Ammonium sulfate was further added to the resulting supernatant so as to give a 45% saturated solution, and thereafter similar procedures were carried out. The resulting precipitate was suspended in 70 ml of 20 mM Tris-HCl (pH 7.5), and dialyzed against the same buffer.

(3) Ion Exchange Chromatography Using Q Sepharose FF

The above dialyzate was centrifuged at 100,000×g for 1 hour to remove insolubles, and thereafter applied onto Q Sepharose FF (Amersham Biotech, column size: 600 ml) equilibrated with 20 mM Tris-HCl (pH 7.5). After washing with the same buffer, LPA phosphatase was eluted with NaCl linear concentration gradient (0–1 M) in 2 liters of the same buffer (FIG. 1). Subsequently, active fractions corresponding to 0.52–0.57 M NaCl were collected, and dialyzed against 20 mM Tris-HCl (pH 7.5).

(4) Ion Exchange Chromatography Using TSK-GEL DEAE-5PW GL

Figure 2:
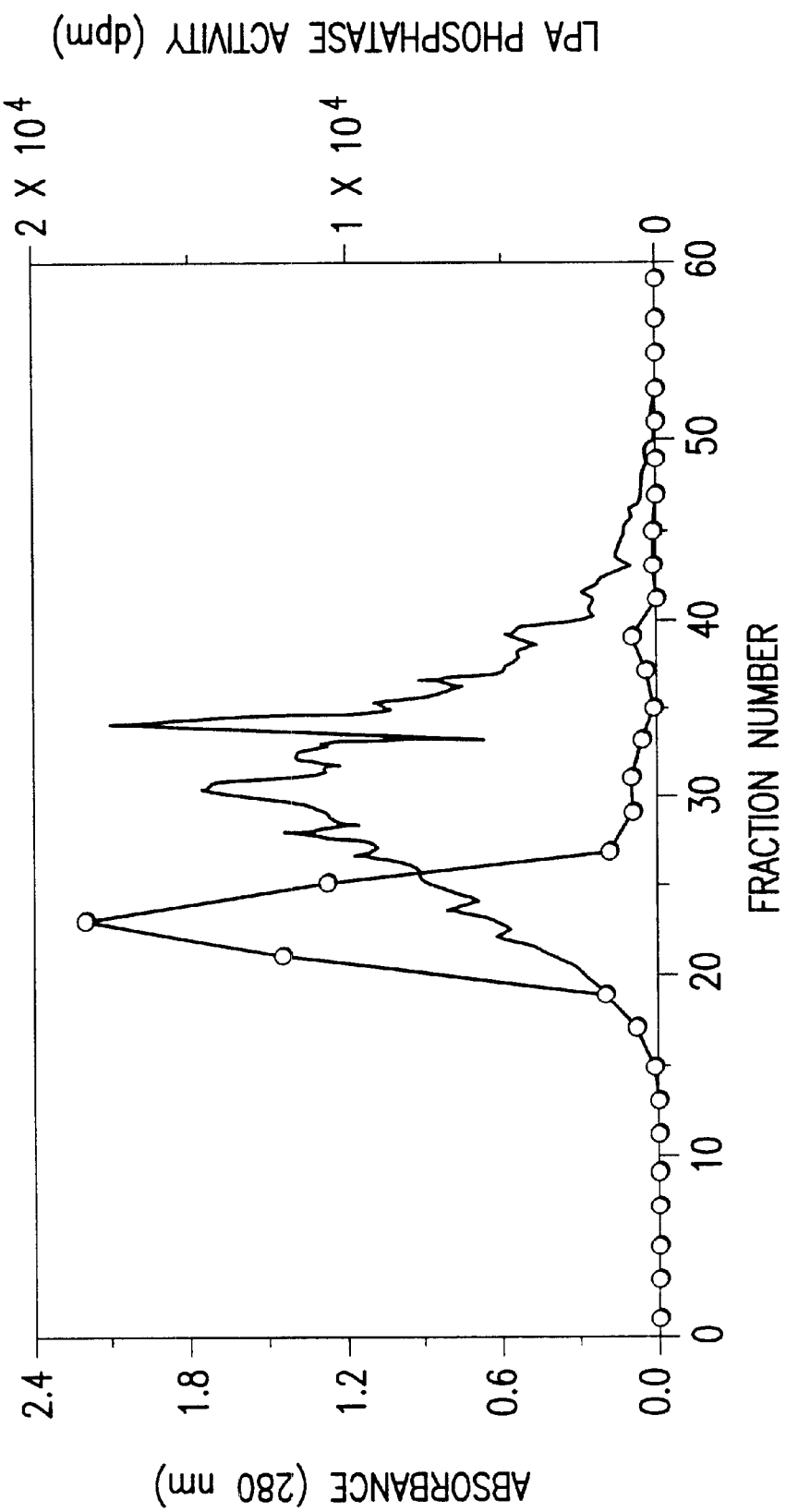
FIG. 2 is a graph showing the results of ion exchange chromatography by TSK-GEL DEAE-5PW GL.

The active fractions obtained by the above ion exchange chromatography were applied onto TSK-GEL DEAE-5PW GL (Tosoh Corporation, column size: 20×150 mm) equilibrated with 20 mM Tris-HCl (pH 7.5). LPA phosphatase was eluted with NaCl linear concentration gradient (0–0.5 M) in 240 ml of the same buffer (FIG. 2). The active fractions (corresponding to 0.16–0.22 M NaCl) were made to be a 60% saturated solution with ammonium sulfate, thereby precipitating.

(5) Gel Filtration Using Hi Load 26/60 Superdex 200

Figure 3:
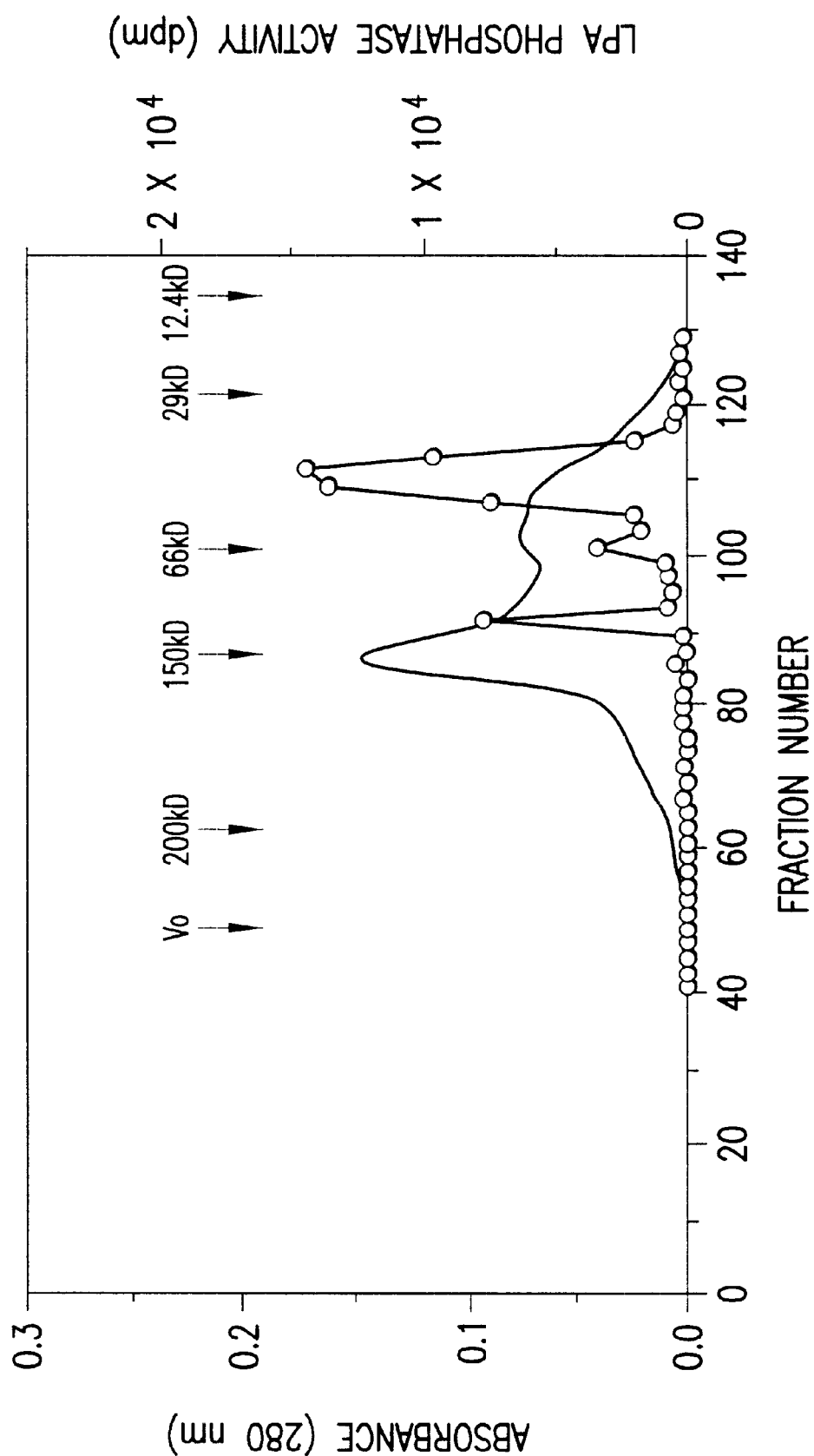
FIG. 3 is a graph showing the results of gel filtration by Hi Load 26/60 Superdex 200.

The above precipitate was dissolved in 3 ml of buffer [20 mM Tris-HCl (pH 7.5), 200 mM NaCl, 0.1% sodium cholate], and the gel filtration was carried out using Hi Load 26/60 Superdex 200 column (Pharmacia Biotech) equilibrated with the same buffer (FIG. 3). The main active fractions were collected and dialyzed against 20 mM MES-NaOH (pH 5.8), to remove sodium cholate.

(6) Adsorption Chromatography Using Hi Trap Heparin Column

Figure 4:
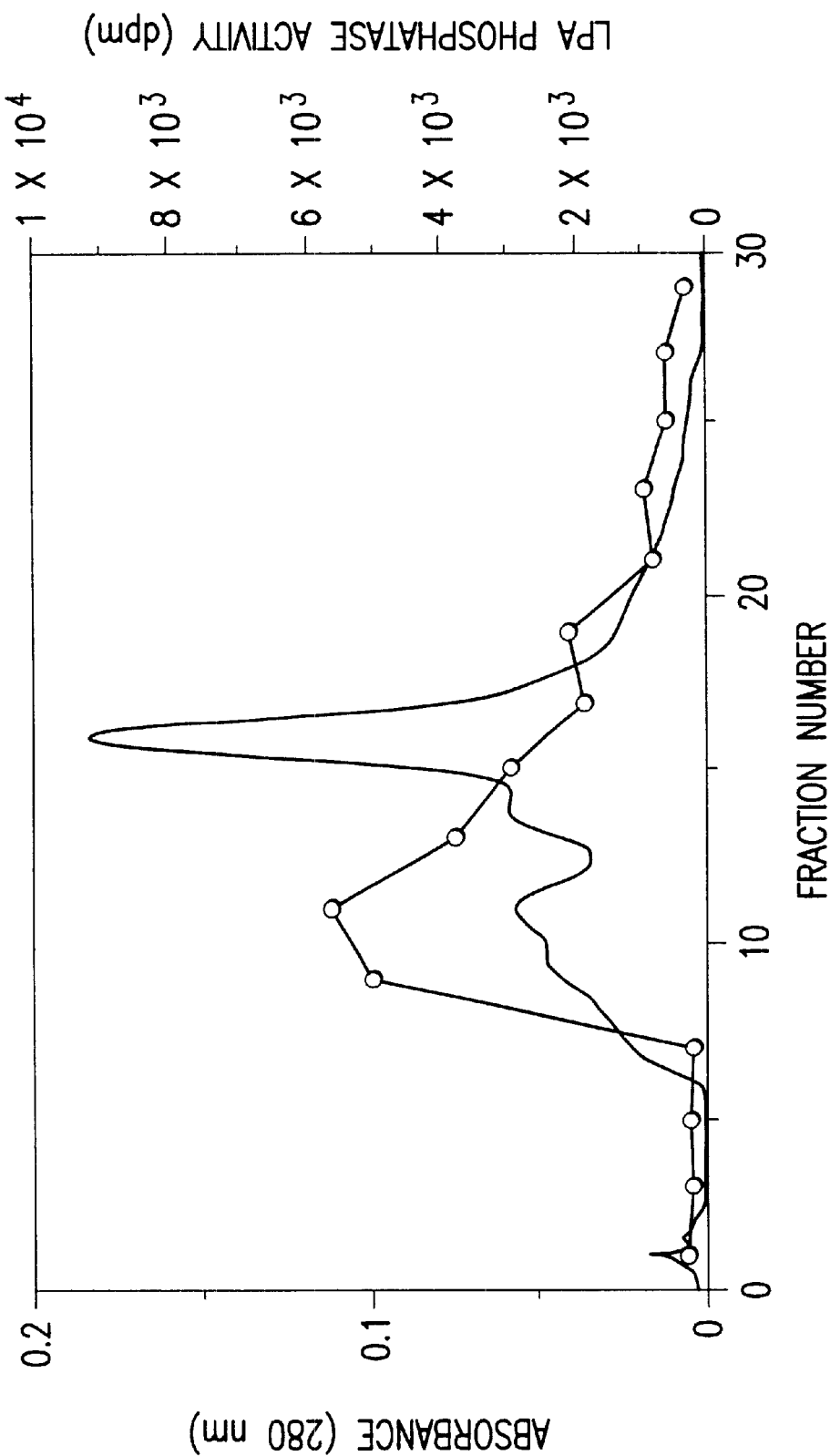
FIG. 4 is a graph showing the results of adsorption chromatography by Hi Trap Heparin column.

The active fractions obtained by the above gel filtration were applied onto Hi Trap Heparin column (Pharmacia Biotech, column size: 1 ml) equilibrated with 20 mM MES-NaOH (pH 5.8). After washing with the same buffer, LPA phosphatase was eluted with NaCl linear concentration gradient (0–1 M) in 30 ml of the same buffer (FIG. 4). As a result, 20 µg of purified enzyme was obtained.

The yield and activity of the LPA phosphatase in each purification step are shown in Table 1. The enzyme activity was determined by the method as described in Test Example 1. It is found from Table 1 that the LPA phosphatase is purified about 3,300-fold.

TABLE 1

| Purification Step | Protein mg | Total Activity units* | Yield % | Specific Activity units/mg | Purification Fold |
|---|---|---|---|---|---|
| 1. Cytosol | 9600 | 3.23 | 100 | 0.00034 | 1 |
| 2. 45% Ammonium Sulfate | 800 | 1.16 | 36.0 | 0.00145 | 4.3 |
| 3. Q-FF | 65.57 | 2.30 | 71.3 | 0.0351 | 104.4 |
| 4. DEAE | 9.25 | 1.60 | 49.7 | 0.1735 | 516.0 |
| 5. Gel Filtration | 1.46 | 0.374 | 11.6 | 0.2558 | 761.0 |
| 6. Heparin | 0.02 | 0.022 | 0.69 | 1.1118 | 3306.9 |

*One unit is defined as an amount of enzyme for catalyzing the formation of 1 micromole of the degradation product in 1 minute.

Test Example 1

Determination of Activity for LPA Phosphatase

The activity for the LPA Phosphatase was determined in 50 µl of a reaction mixture [50 mM Tris-maleic acid (pH 7.5), 50 µM monooleoyl-[9,10-$^3$H]-lysophosphatidic acid (5×10$^4$ dpm), Triton™-X100 at 4-fold molar concentration of the substrate and enzymes at various concentrations]. The above mixture was incubated at 37° C. for 15 minutes, and the enzyme activity was determined by measuring the generated [$^3$H]monooleoylglycerol.

The determination of the enzyme activity at each purification step of Preparation Example 1 was carried out by employing a simple method. Concretely, 250 µl of Dole reagent (isopropanol/heptane/1 N H$_2$SO$_4$=78/28/2) was added to the above enzyme reaction product (50 µl of a mixture) to terminate the reaction, and thereafter 125 µl of H$_2$O and 150 µl of heptane were added thereto. The resulting mixture was mixed and thereafter allowed to separate into two layers by centrifugation at 1,200×g for 5 minutes. The upper layer (150 µl) was taken into another tube, to which 150 µl of heptane and a microspatula amount of silica gel 60H (manufactured by Merck) were then added. After mixing, the mixture was centrifuged at 1,200×g for 5 minutes, and 200 µl of the supernatant was mixed with 2 ml of Scintisol EX-H (manufactured by DOJINDO), and the radioactivity was determined.

The experiment for the specific activity and the reaction rate, and the like is performed by using the following separation method. Concretely, the above enzyme reaction product (50 µl of a mixture) was lyophilized, and monooleoylglycerol was added as a carrier. Thereafter, the mixture was analyzed by thin-layer chromatography (TLC) using a solvent system of n-butanol/acetic acid/water (30.4/4.8/4.8). The TLC plate was exposed to iodine steam, and spots of the monooleoylglycerol were scraped off, and the radioactivity was determined.

Test Example 2

SDS-PAGE

Figure 5:
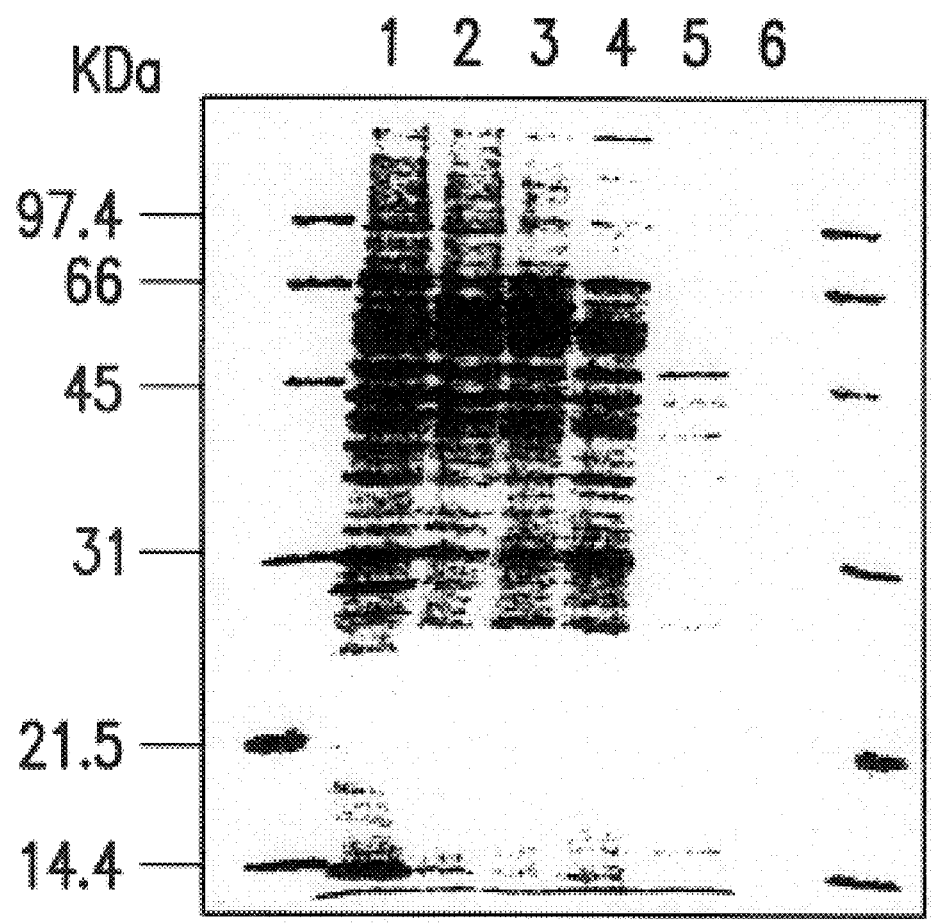
FIG. 5 is a photograph of electrophoresis showing the results of 12.5% SDS-PAGE under reduced conditions. Each of lanes 1 to 6 shows a sample obtained in each step of Example 1 (amount of protein loaded is respectively 14, 10, 5.5, 4.6, 2.1 and 0.27 µg), and the numbers on the left margin indicates a molecular weight of a marker protein.

The enzyme-containing sample obtained in each step of Preparation Example 1 and standard marker for protein (SDS-PAGE Standard Low, manufactured by Bio-Rad) were subjected to SDS-polyacrylamide gel electrophoresis (PAGE) using 12.5% polyacrylamide gel under reduced conditions (FIG. 5).

As shown in FIG. 5, the purified enzyme obtained in the final step showed a single band of about 44 kDa on SDS-PAGE under reducing conditions.

Test Example 3

Substrate Specificity

Each of the enzyme reaction solutions containing various substrates was reacted in the same manner as in Test Example 1, and 25 µl of perchloric acid was added to terminate the reaction. Seventy-five microliters of $H_2O$, 25 µl of 10% ammonium molybdate and 50 µl of 10% ascorbic acid were further added thereto. The mixed solution was boiled at 95° C. for 5 minutes, and thereafter the absorbance at 795 nm was determined to quantify free phosphate.

As a result, the bovine LPA phosphatase strongly hydrolyzed 1-oleoyl-LPA dose-dependently, but did not hydrolyze phosphatidic acid, cardiolipin, bisphosphatidic acid, glycerol phosphate, ceramide 1-phosphate, and sphingosine 1-phosphate.

Figure 6:
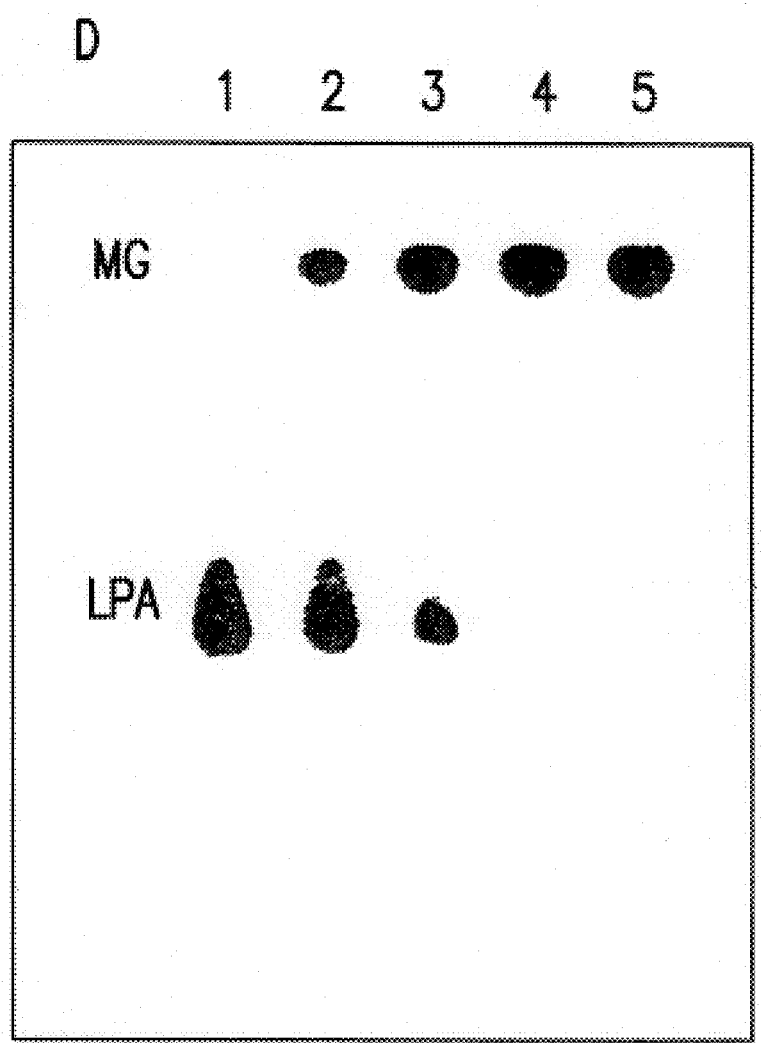
FIG. 6 shows the results of TLC showing that bovine LPA phosphatase dose-dependently hydrolyzes [³H]LPA into [³H]monooleoylglycerol. Lanes 1 to 5 each show an amount of enzyme of 0, 15, 37.5, 75, 150 ng, and MG indicates monooleoylglycerol.

Next, in order to confirm the reactivity with 1-oleoyl-LPA in detail, the enzyme reaction was carried out in the same manner as in Test Example 2 using [$^3$H]1-oleoyl-LPA (5 nmol, 1×10$^5$ dpm) as a substrate, and evaluated by TLC (FIG. 6).

As shown in FIG. 6, the bovine LPA phosphatase hydrolyzed [$^3$H]1-oleoyl-LPA to [$^3$H]1-oleoylglycerol dose-dependently. From this fact, it is found that the enzyme is phosphatase, not phospholipase A.

In order to further confirm in detail the reactivity when 1-oleoyl-LPA and dioleoyl-PA were used as substrates, [$^{32}$P] LPA and [$^{32}$P]PA were used as substrates, which had been labeled by using [γ-$^{32}$P]ATP and *E. coli* DG kinase [Waggoner, D. W. et al., (1996) *J. Biol. Chem.* 271, 16506–16509], and purified with TLC previously. Each of the reactions was carried out by varying the enzyme amount (0–175 ng), or varying the concentration of the substrate (0–100 µM). The enzyme reaction was terminated with 100 µl of 0.1 N hydrochloric acid in methanol solution, and 200 µl of chloroform and 1 M magnesium chloride were each added. The mixture was vigorously mixed, and thereafter centrifuged at 1,000×g for 5 minutes. The radioactivity of 175 µl of the aqueous layer was determined to evaluate the enzyme reaction (FIG. 7).

Figure 7A:
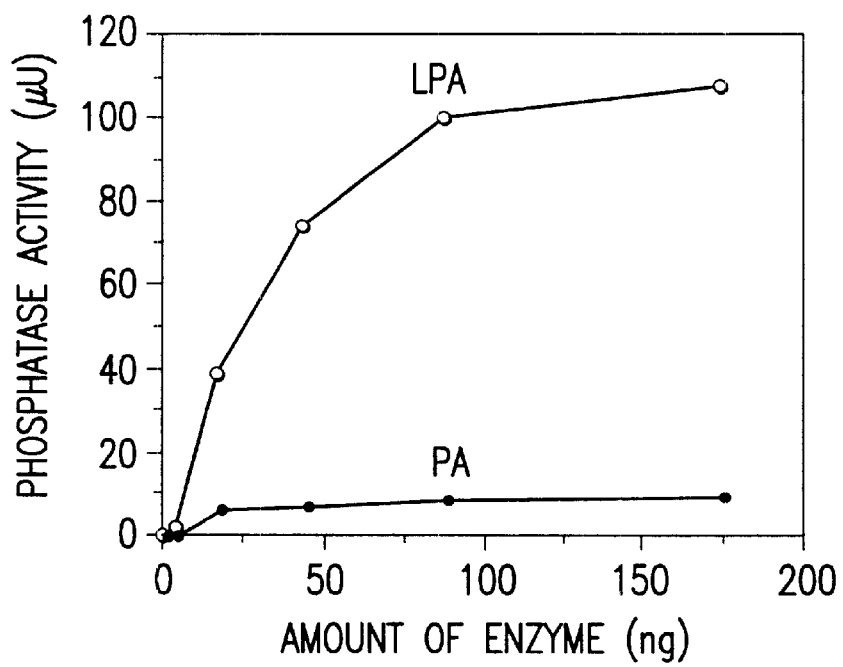
FIG. 7 is a graph for evaluating the reactivity of bovine LPA phosphatase with [³²P]LPA or [³²P] PA, each being previously purified with TLC. Panel A shows the results where amounts of enzyme are changed, and Panel B shows the results where the concentrations of the substrate are changed.
Figure 7B:
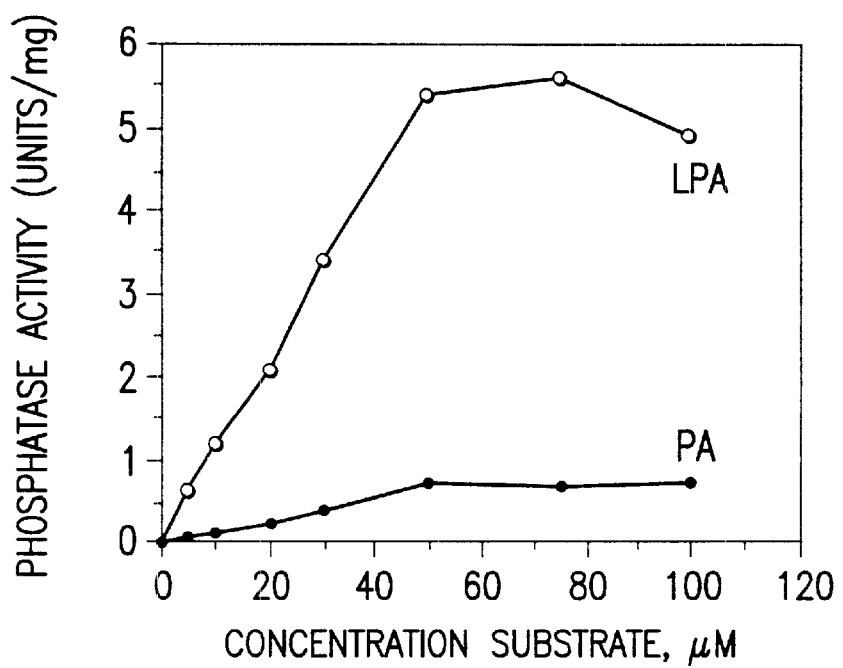

As shown in A and B of FIG. 7, the bovine LPA phosphatase had extremely high reactivity with LPA.

EXAMPLE 1

Determination of Partial Amino Acid Sequence of Bovine LPA Phosphatase

The bovine LPA phosphatase (20 µg) obtained in Preparation Example 1 was subjected to 7.5% SDS-PAGE, and transferred to a PVDF membrane (manufactured by ATTO) by using TRANS-BLOT SD SEMI-DRY TRANSFER CELL (manufactured by Bio-Rad). The membrane was stained with pigment (Ponceau®, manufactured by Tokyo Kasei), and a desired band was cut out. Thereafter, a protein was cleaved with lysylendopeptidase, and extracted with acetonitrile. This extract was fractionated with HPLC C18 column, and 6 peaks were analyzed by Edman degradation method using a peptide sequencer (PPSQ-10 Protein Sequencer, manufactured by SHIMADZU).

As a result, it was found that the above six peptides had the following sequences:
peak 1: MVQVVFRHGARSPL (SEQ ID NO: 3);
peak 2: FLNTISVYTLSPEK (SEQ ID NO: 4);
peak 3: EGPIVISTDEAK (SEQ ID NO: 5);
peak 4: EWFVQLYYRGK (SEQ ID NO: 6);
peak 5: VGMEQMFALGERLRI (SEQ ID NO: 7); and
peak 6: SQLLEVPPQTQLEYTVTNLA (SEQ ID NO: 8).

Among the above sequences, SEQ ID NOs: 3 and 6 had high homology with prostatic acid phosphatase. Therefore, on the basis of these amino acid sequences, there were prepared degenerate oligonucleotide primers:

5'-atggtica(a/g)gtigtitt(t/c)(c/a)gica(t/c)gg-3'   (SEQ ID NO: 9)

and

5'-ccic(g/t)(a/g)ta(a/g)taia(a/g)(t/c)tgiac(a/g)aacca-3'   (SEQ ID NO: 10).

PCR was carried out using the above degenerate primers with DNA of λZAP® II library (derived from human brain cDNA, manufactured by STRATAGENE) as a template. The temperature conditions were:
one cycle of 95° C. for 3 minutes;
40 cycles of 95° C. for 30 seconds, 55° C. for 1 minute, and 72° C. for 2 minutes; and
one cycle of 72° C. for 10 minutes.

The resulting PCR product was subjected to 1% agarose gel electrophoresis, and stained with ethidium bromide, and a band was cut out under UV. The DNA was purified with GENE CLEAN Kit II (manufactured by BIO 101). The purified DNA was blunt-ended with T4 polynucleotide kinase (manufactured by NEW ENGLAND Biolabs) and Klenow fragment (manufactured by TAKARA) of DNA polymerase I. The blunt-ended fragment was subcloned into pBluescript® II KS(–) (manufactured by STRATAGENE) cleaved with SmaI restriction endonuclease (manufactured by TAKARA).

The pBluescript® II KS(–) carrying the subcloned DNA was transformed into JM 109 competent cells, and a DNA was isolated from the resulting transformant, and sequenced with a DNA sequencer (dNA sequencer LONG READIR 4200, manufactured by Aloka) by using the Thermo Sequenase fluorescence labeled-primer cycle sequence kit (manufactured by Amersham) comprising 7-deaza-dGTP, M13 forward primer and M13 reverse primer (manufactured by LI-COR).

As a result, it was found that a cDNA fragment of 987 bp was cloned.

Next, the above λZAP® II library was screened by colony hybridization method with the above fragment of 987 bp as a probe. Concretely, as a primary screening, a total of 1×10$^6$ colonies (host cells: XL-1-Blue) were spread on 20 sheets of 15 cm agar culture plates. The grown colonies were transferred to Colony/Plaque Screen Hybridization Transfer Membrane (manufactured by NEN). The membrane was subjected to hybridization under usual hybridization conditions at 65° C. with the above fragment of 987 bp as a probe, labeled with $^{32}$p using Klenow fragment of DNA polymerase I.

Twenty four positive clones were picked up by autoradiography, and a secondary screening was carried out by repeating the same procedures as the above primary screening.

Twenty positive clones were picked up by autoradiography, and in vivo excision manipulation using a helper phage was carried out in accordance with the manual of λZAP® II library, to give a cDNA cloned into pBluescript® II SK(–).

The resulting CDNA derived from the 20 clones was sequenced in the same manner as above, and a clone carrying a CDNA having the longest length of 1731 bp was obtained. This nucleotide sequence is shown in SEQ ID NO: 2. The nucleotide sequence carries a coding region of 1263 bp, and an amino acid sequence encoded thereby is shown in SEQ ID NO: 1. The cloned LPA phosphatase derived from human comprises a signal peptide consisting of 40 amino acid residues at N-terminal, and was a novel phosphatase having 421 amino acid residues. When the amino acid sequence of the human LPA phosphatase of the present invention was compared with a known phosphatase, it was homologous to acid phosphatase, particularly showing high homology in an active region.

EXAMPLE 2

Expression of Human LPA Phosphatase in *E. coli*

The human LPA phosphatase obtained in Example 1 comprises a signal peptide at N-terminal. When the protein was expressed in *E. coli*, there is a possibility that the signal peptide is cleaved. When a protein resulting from fusion of N-terminal of the human LPA phosphatase with other proteins is expressed in *E. coli* and purified, there are deduced the difficulty of purification caused by cleavage of the signal peptide and the lowering of the phosphatase activity. Therefore, in this example, a construct carrying a sequence encoding a signal peptide and a construct without such a sequence were prepared.

PCR was carried out with LPA phosphatase cDNA cloned into pBluescript® II SK(−) obtained by the secondary screening of Example 1 as a template, by using the following primers:
(1) Without Signal Peptide forward: 5'-(cgcggatcc)ctgaagttgaaaatggtgcag-3'  (SEQ ID NO: 11)

reverse: 5'-(cgcggatcc)agttactcttcatttccaacttc-3'  (SEQ ID NO: 12)

(2) With Signal Peptide forward: 5'-(cgcggatcc)atgcgcttgtggaccccag-3'  (SEQ ID NO: 13)

reverse: 5'-(cgcggatcc)agttactcttcatttccaacttc-3'  (SEQ ID NO: 12)

wherein "ggatcc" in the parentheses indicates BamHI site.
The temperature cycles consisted of:
95° C. for 3 minutes;
10 cycles of 95° C. for 30 seconds, 55° C. for 1 minute, and 72° C. for 2 minutes;
30 cycles of 95° C. for 30 seconds and 72° C. for 2 minutes; and
72° C. for 10 minutes.

Two kinds of the PCR amplified products were cleaved with BamHI restriction endonuclease (manufactured by NEW ENGLAND Biolabs), and subjected to 1% agarose gel electrophoresis. The gel was stained with ethidium bromide, and thereafter a band was cut out under UV. A DNA fragment was purified by GENE CLEAN Kit II (manufactured by BIO 101), and the purified fragment was subdoned into pBluescript® II KS(−) (manufactured by STRATAGENE) cleaved with BamHI restriction endonuclease (manufactured by TAKARA).

The cloned DNA fragment was sequenced in the same manner as in Example 1 and confirmed, and thereafter a DNA fragment cut out with BamHI restriction endonuclease was ligated with pGEX-2T (manufactured by Pharmacia Biotech) cleaved with BamHI restriction endonuclease.

Two kinds of the resulting expression constructs were transformed into JM109 competent cells, to give a transformant. The transformant in the logarithmic growth phase (in 200 ml of L medium) was cultured at 25° C. for 4 hours. Thereafter, 400 µl of 1 M IPTG was added thereto, and the mixture was cultured for additional 2 hours. The culture was centrifuged at 4° C., 8000 rpm for 15 minutes, to harvest the bacterial cells. Five milliliters of buffer [50 mM Tris-HCl (pH 7.6), 1 mM EDTA] was added thereto, and the bacterial cells were disrupted by sonication treatment, followed by centrifugation at 4° C., 15000 rpm for 30 minutes, to give a supernatant.

The resulting supernatant was mixed with glutathione beads (Glutathione Sepharose® 4B, manufactured by Pharmacia Biotech) previously equilibrated with the above buffer, and the mixture was stirred overnight at 4° C. The beads were washed with Dulbecco phosphate buffer PBS(−) containing 0.5 M NaCl, and thereafter eluted with 200 µl of glutathione solution three times.

Ten microliters of the eluate was subjected to 12.5% SDS-PAGE, and stained with Coomassie brilliant blue, and as a result, the GST-LPA phosphatase of a desired size (about 71 kDa) was confirmed. In addition, there were no differences in the expression levels by the presence or absence of the signal peptide.

Five microliters of the above eluate was assayed for the LPA phosphatase activity in accordance with the method described in Test Example 1. As a result, the GST-LPA phosphatase exhibited the same level of LPA phosphatase activity, regardless of the presence or absence of the signal peptide.

EXAMPLE 3

Preparation of 6×His-Tagged LPAP

*E. coli* was selected as host cells, and pQE-30 (QIAGEN) was used as an expression vector.

PCR was carried out with the LPA phosphatase cDNA cloned into pBluescript® II SK(−) obtained by the secondary screening of Example 1 as a template, by using the following primers:

forward: 5'-(cgcggatcc)ctgaagttgaaaatggtgcag-3'  (SEQ ID NO: 11)

reverse: 5'-(cgcggatcc)agttactcttcatttccaacttc-3'  (SEQ ID NO: 12)

wherein "ggatcc" in the parentheses indicates BamHI site.
The temperature cycles consisted of:
95° C. for 3 minutes;
10 cycles of 95° C. for 30 seconds, 55° C. for 1 minute, and 72° C. for 2 minutes;
30 cycles of 95° C. for 30 seconds and 72° C. for 2 minutes; and
72° C. for 10 minutes.

The resulting PCR amplified product was cleaved with BamHI restriction endonuclease (manufactured by NEW ENGLAND Biolabs), and subjected to 1% agarose gel electrophoresis. The gel was stained with ethidium bromide, and thereafter the band was cut out under UV. A DNA fragment was purified by GENE CLEAN Kit II (manufactured by BIO 101), and the purified fragment was subcloned into pBluescript® II KS(−) (manufactured by STRATAGENE) cleaved with BamHI restriction endonuclease (manufactured by TAKARA).

The subdoned DNA fragment was sequenced and confirmed to be identical, and thereafter, the DNA insert cut out with BamHI restriction endonuclease was ligated with pQE-30 (QIAGEN) cleaved with BamHI.

JM109 competent cells were transformed with the resulting expression construct, to give a transformant. The transformant in the logarithmic growth phase (in 200 ml of L medium) was cultured at 25° C. for 4 hours. Thereafter, 400 µl of 1 M IPTG was added thereto, and the mixture was cultured for additional 2 hours. The culture was centrifuged at 4° C., 8000 rpm for 15 minutes, to harvest the bacterial cells. Five milliliters of buffer [50 mM $NaH_2PO_4$, 300 mM NaCl (pH 8.0)] was added thereto, and the bacterial cells were disrupted by sonication treatment, followed by centrifugation at 4° C., 15000 rpm for 30 minutes, to give a supernatant.

The resulting supernatant was mixed with Ni-NTA agarose (QIAGEN) previously equilibrated with the above buffer, and the mixture was stirred overnight at 4° C. The agarose was washed with washing buffer [50 mM $NaH_2PO_4$, 300 mM NaCl, 10% glycerol (pH 6.0)], and thereafter eluted three times with 200 μl of an eluent (prepared by adding 250 mM imidazole to the washing buffer).

The eluent was subjected to 12.5% SDS-PAGE, and stained with Coomassie brilliant blue, and as a result, the 6xHis-tagged LPAP of a desired size (about 44 kDa) was confirmed.

The expressed 6xHis-tagged LPAP could be purified by Ni-NTA (nickel nitrilotriacetate) matrix having extremely high affinity with 6xHis-tagged protein.

EXAMPLE 4

Preparation of Determination Reagent

The following determination reagents (Reagent A, Reagent B) were prepared.

Reagent A

| | |
|---|---|
| Buffer (0.1 M Tris) | 100 mmol/l |
| Nonionic Surfactant (Triton X-100) | 0.01% by wt. |
| $NAD^+$ | 2 mmol/l |
| Inosine | 5 mmol/l |
| Purine-Nucleoside Phosphorylase | 1 U/ml |
| Xanthine Dehydrogenase | 2 U/ml |
| pH 8.2 | |

Reagent B

| | |
|---|---|
| Buffer (0.1 M Tris) | 100 mmol/l |
| Nonionic Surfactant (Triton X-100) | 0.01% by wt |
| Recombinant LPA Phosphatase | 0.08 mg/ml |
| pH 8.2 | (6 mU/ml) |

The 1-oleoyl-LPA was dissolved in physiological saline containing a surfactant (Triton X-100), to give a sample so as to have a final concentration of about 0.1, 0.2, or 0.3 mmol/l.

Figure 8:
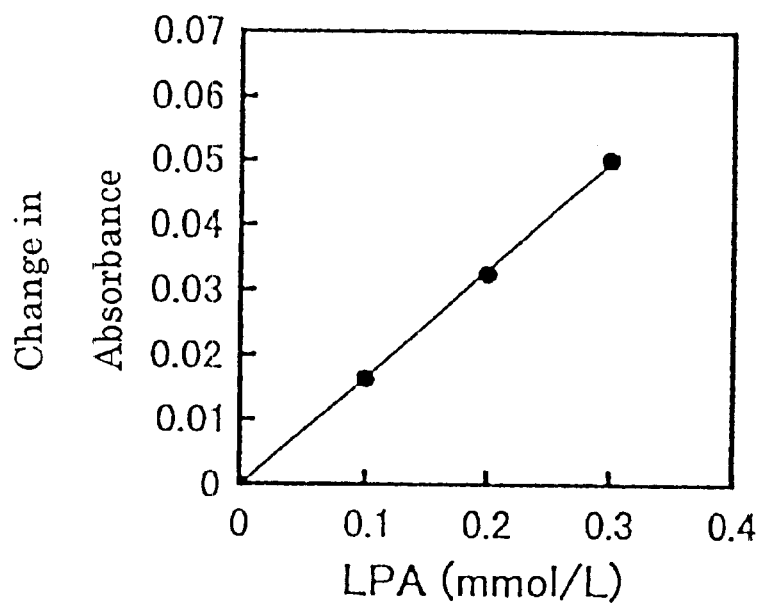
FIG. 8 is a drawing showing a calibration curve for the LPA determination, which is obtained by using a determination reagent of the present invention. The upper panel shows changes in absorbances when a sample of each LPA concentration is determined. The lower panel shows a graph of the calibration curve prepared on the basis of the obtained values of changes in absorbances.

Two-hundred and forty microliters of Reagent A was added to 8 μl of the sample, and the mixture was reacted at 37° C. for 5 minutes. Thereafter, 80 μl of Reagent B was added thereto, and the mixture was further reacted at 37° C. for 5 minutes. The change in the absorbance at a wavelength of 340 nm for 5 minutes after adding Reagent B was determined using reagent blank as a control. Purified water was used as a sample for the reagent blank. As shown in FIG. 8, a calibration curve passing through the origin was obtained.

EXAMPLE 5

Preparation of Determination Reagent

The following determination reagents (Reagent a, Reagent b) were prepared.

Reagent a

| | |
|---|---|
| Buffer (0.1 M HEPES) | 100 mmol/l |
| Nonionic Surfactant (Triton X-100) | 0.01% by wt. |
| Peroxidase | 10 U/ml |
| Purine-Nucleoside Phosphorylase | 0.5 U/ml |
| Xanthine Oxidase | 3 U/ml |
| Inosine | 3 mmol/l |
| N-Ethyl-N-(2-hydroxy-3-sulfopropyl)-3 methylaniline | 5 mmol/l |
| pH 7.7 | |

Reagent b

| | |
|---|---|
| Buffer (0.1 M HEPES) | 100 mmol/l |
| Nonionic Surfactant (Triton X-100) | 0.01% by wt |
| 4-Aminoantipyrine | 10 mmol/l |
| Recombinant LPA Phosphatase | 0.08 mg/ml |
| pH 7.7 | (6 mU/ml) |

Each of the various LPAs such as 1-palmitoyl-LPA, 1-stearoyl-LPA, 1-oleoyl-LPA, 2-oleoyl-LPA, 1-linoleoyl-LPA and 1-arachidonoyl-LPA was dissolved in physiological saline containing a surfactant, to prepare a 0.2 mmol/l sample. Two-hundred and forty microliters of Reagent a was added to 8 μl of the sample, and the mixture was reacted at 37° C. for 5 minutes. Thereafter, 80 μl of Reagent b was added thereto, and the mixture was further reacted at 37° C. for 5 minutes. The change in the absorbance at a wavelength of 570 nm for 5 minutes after adding Reagent b was determined using reagent blank as a control.

Figure 9:
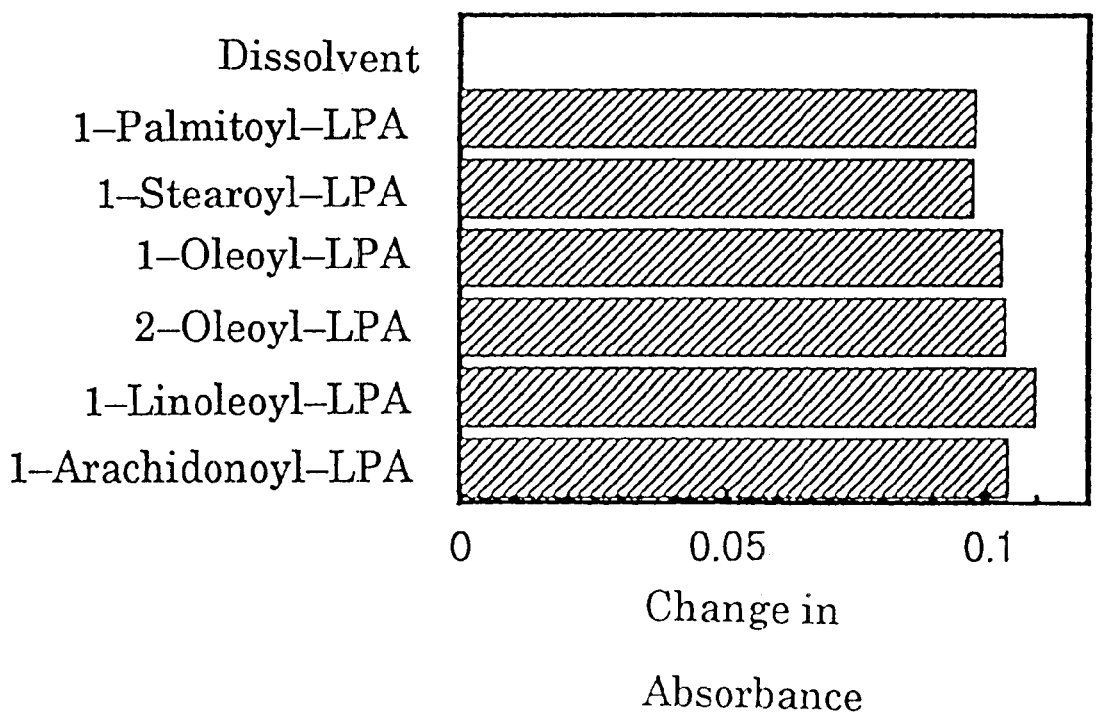
FIG. 9 is a drawing showing the results for determination of various kinds of LPA wherein fatty acid moieties in the acyl group are different. The upper panel shows changes in absorbances determined for each sample; and the lower panel shows a graph prepared on the basis of the obtained values of changes in absorbances.
Figure 10:
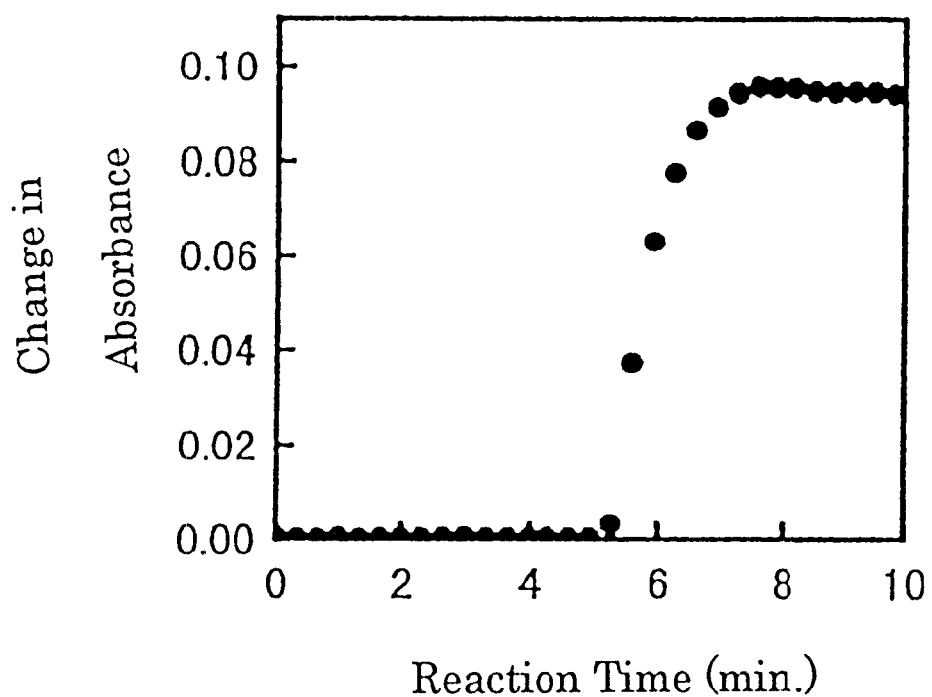
FIG. 10 is a graph showing results of the reaction time course for 1-oleoyl-LPA determined by using a determination reagent of the present invention.

As shown in FIG. 9, using the present determination reagent, it is made possible to assay various LPAs having different kinds of fatty acids in acyl group. The reaction time course for 1-oleoyl-LPA is shown in FIG. 10. The absorbance dramatically increases after addition of reagent b, reaching a peak in several minutes. In addition, each of various phospholipids such as 1,2-dipalmitoylphosphatidic acid (1,2-dipalmitoyl-PA), 1-palmitoylphosphatidylethanolamine (1-palmitoyl-LPE), and 1-palmitoylphosphatidylcholine (1-palmitoyl-LPC) was dissolved in physiological saline containing a surfactant, to prepare a 0.2 mmol/l sample. The absorbance was determined by the same procedures.

Figure 11:
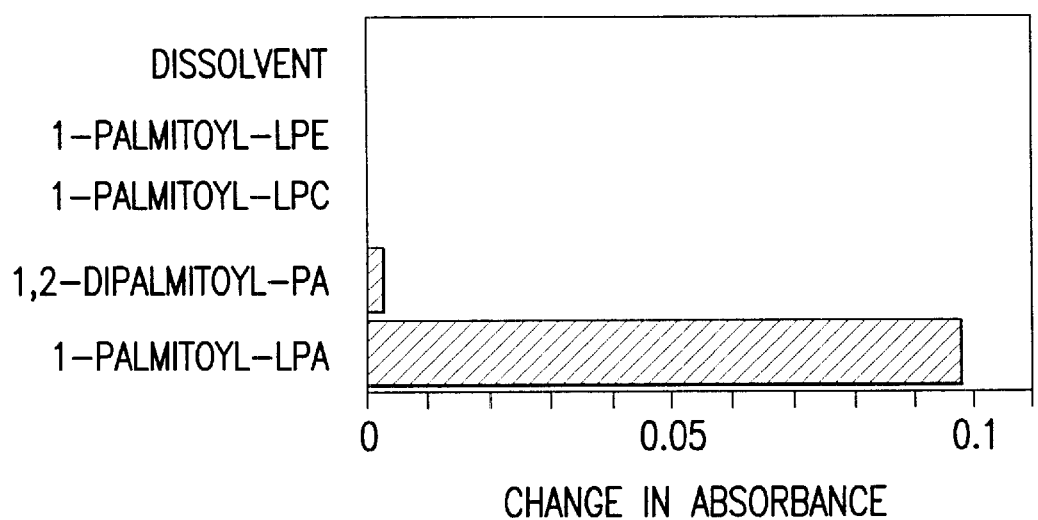
FIG. 11 is a drawing showing the results of determination of a sample containing LPA, PA, LPE or LPC using a determination reagent of the present invention.

As shown in FIG. 11, when using the present determination reagent, the LPA is specifically assayed, and other phospholipids such as PA, LPA and LPC cannot substantially be done.

Further, the change in the absorbance was determined by the same procedures for each of commercially available control sera, 0.2 mM 1-oleoyl-LPA, and one prepared by adding 1-oleoyl-LPA to the commercially available control serum so as to be 0.2 mM. The determination accuracy (%) of LPA was calculated from each of the obtained changes in the absorbance by the following equation:

$$\text{Determination Accuracy} = \frac{\begin{bmatrix} \text{Change in} \\ \text{Absorbance of} \\ \text{Mixture of} \\ \text{Commercially} \\ \text{Available Control} \\ \text{Serum and} \\ \text{1-Oleoyl-LPA} \end{bmatrix}}{\begin{bmatrix} \text{Change in} \\ \text{Absorbance of} \\ \text{Commercially} \\ \text{Available} \\ \text{Control Serum} \end{bmatrix} + \begin{bmatrix} \text{Change in} \\ \text{Absorbance of} \\ \text{1-Oleoyl-LPA} \end{bmatrix}} \times 100$$

Here, the determination accuracy is higher if the value approximates 100. The results are shown in Table 2.

TABLE 2

|  | Changes in Absorbance |
|---|---|
| Commercially Available Control Serum | 0.0982 |
| 0.2 mmol/l 1-Oleoyl-LPA | 0.0988 |
| Commercially Available Control Serum + 0.2 mmol/l 1-Oleoyl-LPA | 0.1976 |

Determination Accuracy (%) = 100.3

It is shown from the results of Table 2 that the determination accuracy is 100.3%, so that even if the sample is LPA in serum, it can be assayed without being affected by other serum components.

EQUIVALENTS

The present invention can be embodiment in any other forms without departing from the spirit or essential characteristics of the invention. Therefore, the above-described examples are merely illustration in all aspects, and should not be understood to be limited thereto. The scope of the present invention is given in the claims, and is not bound to the description of the specification. Further, all modifications and changes belonging to the scope of equivalency of the claims are intended to be embraced within the scope of the present invention.

INDUSTRIAL APPLICABILITY

According to the present invention, there are provided a recombinant LPA phosphatase capable of specifically hydrolyzing the LPA, and the like. In addition, according to the present invention, the metabolic pathway of the LPA is elucidated, and further various diseases involving the LPA or LPA phosphatase can be diagnosed and treated. Moreover, according to the present invention the determination of the LPA a promising index for diseases and the like in the field of clinical testing can be more simply carried out without necessitating complicated procedures as in the conventional methods, and the determination can be made for a large number of samples to be analyzed, so that it can be applied to conventional biochemical automatic analyzer, thereby being highly useful.

---

What is claimed is:

1. A protein encoded by a DNA, wherein the DNA is selected from the group consisting of:
   (a) a DNA encoding a peptide comprising the amino acid sequence of SEQ ID NO: 1;
   (b) a DNA comprising the nucleotide sequence of SEQ ID NO: 2; and
   (c) a DNA capable of hybridizing to the DNA of any one of the above (a) or (b), under stringent conditions, wherein said stringent conditions are heating at 42° C. in a solution containing 6×SSC, 0.5% SDS, and 50% formamide, following by washing at 68° C. in a solution containing 0.1×SSC and 0.5% SDS.

2. A method for determination of LPA, comprising the step of mixing the protein of claim 1 with a sample to be tested.

3. The method for determination of LPA according to claim 2, wherein the presence or absence of a product resulting from hydrolysation of lysophosphatidic acid by the protein of claim 2 is used as an index of the presence or absence of lysophosphatidic acid.

4. The method for determination of LPA according to claim 3, wherein phosphoric acid or monoacyl glycerol is determined as the hydrolysate of lysophosphatidic acid.

5. A composition for the determination of lysophosphatidic acid (LPA), comprising the protein of claim 1.

6. The composition according to claim 2, further comprising a reagent for determining phosphoric acid or monoacyl glycerol.

7. A kit for diagnosing a disease in which LPA is involved, comprising the composition of claim 5 or 6, wherein said disease is selected from the group consisting of ovarian cancer, peritoneal cancer, endometrial cancer and endocervical cancer.

* * * * *

SEQUENCE LISTING

<160> NUMBER OF SEQ ID NOS: 13

<210> SEQ ID NO 1
<211> LENGTH: 421
<212> TYPE: PRT
<213> ORGANISM: Homo sapiens
<220> FEATURE:
<221> NAME/KEY: SIGNAL
<222> LOCATION: (1)..(40)
<223> OTHER INFORMATION: sig peptide

<400> SEQUENCE: 1

Met Arg Leu Trp Thr Pro Val Gly Val Leu Thr Ser Leu Ala Tyr Cys
 1               5                  10                  15

Leu His Gln Arg Arg Val Ala Leu Ala Glu Leu Gln Glu Ala Asp Gly
                20                  25                  30

Gln Cys Pro Val Asp Arg Ser Leu Leu Lys Leu Lys Met Val Gln Val
            35                  40                  45

Val Phe Arg His Gly Ala Arg Ser Pro Leu Lys Pro Leu Pro Leu Glu
        50                  55                  60

Glu Gln Val Glu Trp Asn Pro Gln Leu Leu Glu Val Pro Pro Gln Thr
    65                  70                  75                  80

Gln Phe Asp Tyr Thr Val Thr Asn Leu Ala Gly Gly Pro Lys Pro Tyr
                85                  90                  95

Ser Pro Tyr Asp Ser Gln Tyr His Glu Thr Thr Leu Lys Gly Gly Met
            100                 105                 110

Phe Ala Gly Gln Leu Thr Lys Val Gly Met Gln Gln Met Phe Ala Leu
        115                 120                 125

Gly Glu Arg Leu Arg Lys Asn Tyr Val Glu Asp Ile Pro Phe Leu Ser
    130                 135                 140
Pro Thr Phe Asn Pro Gln Glu Val Phe Ile Arg Ser Thr Asn Ile Phe
145                 150                 155                 160
Arg Asn Leu Glu Ser Thr Arg Cys Leu Leu Ala Gly Leu Phe Gln Cys
                165                 170                 175
Gln Lys Glu Gly Pro Ile Ile Ile His Thr Asp Glu Ala Asp Ser Glu
            180                 185                 190
Val Leu Tyr Pro Asn Tyr Gln Ser Cys Trp Ser Leu Arg Gln Arg Thr
        195                 200                 205
Arg Gly Arg Arg Gln Thr Ala Ser Leu Gln Pro Gly Ile Ser Glu Asp
    210                 215                 220
Leu Lys Lys Val Lys Asp Arg Met Gly Ile Asp Ser Ser Asp Lys Val
225                 230                 235                 240
Asp Phe Phe Ile Leu Leu Asp Asn Val Ala Ala Glu Gln Ala His Asn
                245                 250                 255
Leu Pro Ser Cys Pro Met Leu Lys Arg Phe Ala Arg Met Ile Glu Gln
            260                 265                 270
Arg Ala Val Asp Thr Ser Leu Tyr Ile Leu Pro Lys Glu Asp Arg Glu
        275                 280                 285
Ser Leu Gln Met Ala Val Gly Pro Phe Leu His Ile Leu Glu Ser Asn
    290                 295                 300
Leu Leu Lys Ala Met Asp Ser Ala Thr Ala Pro Asp Lys Ile Arg Lys
305                 310                 315                 320
Leu Tyr Leu Tyr Ala Ala His Asp Val Thr Phe Ile Pro Leu Leu Met
                325                 330                 335
Thr Leu Gly Ile Phe Asp His Lys Trp Pro Pro Phe Ala Val Asp Leu
            340                 345                 350
Thr Met Glu Leu Tyr Gln His Leu Glu Ser Lys Glu Trp Phe Val Gln
    355                 360                 365
Leu Tyr Tyr His Gly Lys Glu Gln Val Pro Arg Gly Cys Pro Asp Gly
        370                 375                 380
Leu Cys Pro Leu Asp Met Phe Leu Asn Ala Met Ser Val Tyr Thr Leu
385                 390                 395                 400
Ser Pro Glu Lys Tyr His Ala Leu Cys Ser Gln Thr Gln Val Met Glu
                405                 410                 415
Val Gly Asn Glu Glu
            420

<210> SEQ ID NO 2
<211> LENGTH: 1731
<212> TYPE: DNA
<213> ORGANISM: Homo sapiens
<220> FEATURE:
<221> NAME/KEY: CDS
<222> LOCATION: (397)...(1659)

<400> SEQUENCE: 2
ggaactcagg gccggctcct gttccttcaa gagtgctgga ggccaaactt gaaatacaag      60
tttaatgttc ctcgtcgggc aaaagataag gatccgatct ccccggccc ggtgtgcagc     120 aggagcgacc aaccccgacc cgggttaaaa ctcccaggga ctcttcgctg ctgccacctc    180
ttgttctctc cccgttccc actcgggtc tccctcaggg ccgggaggca cagcggtccc      240
tgcttgctga agggctggat gtacgcatcc gcaggttccc gcggacttgg gggcgcccgc    300

```
tgagccccgg cgcccgcaga agacttgtgt ttgcctcctg cagcctcaac ccggaggcag      360
cgagggccta ccaccatgat cactggtgtg ttcagcatgc gcttgtggac cccagtgggc      420
gtcctgacct cgctggcgta ctgcctgcac cagcggcggg tggccctggc cgagctgcag      480
gaggccgatg ccagtgtcc ggtcgaccgc agcctgctga agttgaaaat ggtgcaggtc       540
gtgtttcgac acgggctcg gagtcctctc aagccgctcc cgctggagga gcaggtagag       600
tggaaccccc agctattaga ggtcccaccc caaactcagt ttgattacac agtcaccaat      660
ctagctggtg gtccgaaacc atattctcct tacgactctc aataccatga gaccaccctg      720 aagggggggca tgtttgctgg gcagctgacc aaggtgggca tgcagcaaat gtttgccttg    780
ggagagagac tgaggaagaa ctatgtggaa gacattccct ttctttcacc aaccttcaac     840
ccacaggagg tctttattcg ttccactaac attttcgga atctggagtc caccgttgt        900 ttgctggctg gcttttcca gtgtcagaaa gaaggaccca tcatcatcca cactgatgaa      960
gcagattcag aagtcttgta tcccaactac caaagctgct ggagcctgag gcagagaacc    1020
agaggccgga ggcagactgc ctctttacag ccaggaatct cagaggattt gaaaaaggtg    1080
aaggacagga tgggcattga cagtagtgat aaagtggact tcttcatcct cctggacaac   1140
gtggctgccg agcaggcaca caacctccca agctgcccca tgctgaagag atttgcacgg    1200
atgatcgaac agagagctgt ggacacatcc ttgtacatac tgcccaagga agacagggaa    1260
agtcttcaga tggcagtagg cccattcctc cacatcctag agagcaacct gctgaaagcc    1320
atggactctg ccactgcccc cgacaagatc agaaagctgt atctctatgc ggctcatgat   1380
gtgaccttca taccgctctt aatgaccctg gggattttg accacaaatg ccaccgtttt     1440
gctgttgacc tgaccatgga actttaccag cacctggaat ctaaggagtg gtttgtgcag    1500
ctctattacc acgggaagga gcaggtgccg agaggttgcc ctgatgggct ctgcccgctg    1560
gacatgttct tgaatgccat gtcagtttat accttaagcc cagaaaaata ccatgcactc    1620
tgctctcaaa ctcaggtgat ggaagttgga aatgaagagt aactgattta taaaagcagg    1680
atgtgttgat tttaaaataa agtgccttta tacaaaaaaa aaaaaaaaa a               1731
```

<210> SEQ ID NO 3
<211> LENGTH: 14
<212> TYPE: PRT
<213> ORGANISM: Bovine

<400> SEQUENCE: 3

Met Val Gln Val Val Phe Arg His Gly Ala Arg Ser Pro Leu
 1               5                  10

<210> SEQ ID NO 4
<211> LENGTH: 14
<212> TYPE: PRT
<213> ORGANISM: Bovine

<400> SEQUENCE: 4

Phe Leu Asn Thr Ile Ser Val Tyr Thr Leu Ser Pro Glu Lys
 1               5                  10

<210> SEQ ID NO 5
<211> LENGTH: 12
<212> TYPE: PRT
<213> ORGANISM: Bovine

<400> SEQUENCE: 5

Glu Gly Pro Ile Val Ile Ser Thr Asp Glu Ala Lys

```
<210> SEQ ID NO 6
<211> LENGTH: 11
<212> TYPE: PRT
<213> ORGANISM: Bovine

<400> SEQUENCE: 6

Glu Trp Phe Val Gln Leu Tyr Tyr Arg Gly Lys
 1               5                  10

<210> SEQ ID NO 7
<211> LENGTH: 15
<212> TYPE: PRT
<213> ORGANISM: Bovine

<400> SEQUENCE: 7

Val Gly Met Glu Gln Met Phe Ala Leu Gly Glu Arg Leu Arg Ile
 1               5                  10                  15

<210> SEQ ID NO 8
<211> LENGTH: 20
<212> TYPE: PRT
<213> ORGANISM: Bovine

<400> SEQUENCE: 8

Ser Gln Leu Leu Glu Val Pro Pro Gln Thr Gln Leu Glu Tyr Thr Val
 1               5                  10                  15

Thr Asn Leu Ala
            20

<210> SEQ ID NO 9
<211> LENGTH: 26
<212> TYPE: DNA
<213> ORGANISM: Artificial Sequence
<220> FEATURE:
<223> OTHER INFORMATION: oligonucleotide primer
<221> NAME/KEY: modified_base
<222> LOCATION: (1)..(26)
<223> OTHER INFORMATION: any n = i

<400> SEQUENCE: 9
atggtncarg tngtnttymg ncaygg                                      26

<210> SEQ ID NO 10
<211> LENGTH: 26
<212> TYPE: DNA
<213> ORGANISM: Artificial Sequence
<220> FEATURE:
<223> OTHER INFORMATION: oligonucleotide primer
<221> NAME/KEY: modified_base
<222> LOCATION: (1)..(26)
<223> OTHER INFORMATION: any n = i

<400> SEQUENCE: 10
ccnckrtart anarytgnac raacca                                      26

<210> SEQ ID NO 11
<211> LENGTH: 30
<212> TYPE: DNA
<213> ORGANISM: Artificial Sequence
<220> FEATURE:
<223> OTHER INFORMATION: oligonucleotide PCR primer

<400> SEQUENCE: 11
cgcggatccc tgaagttgaa aatggtgcag                                  30
```

```
<210> SEQ ID NO 12
<211> LENGTH: 32
<212> TYPE: DNA
<213> ORGANISM: Artificial Sequence
<220> FEATURE:
<223> OTHER INFORMATION: oligonucleotide PCR primer

<400> SEQUENCE: 12
cgcggatcca gttactcttc atttccaact tc                              32

<210> SEQ ID NO 13
<211> LENGTH: 28
<212> TYPE: DNA
<213> ORGANISM: Artificial Sequence
<220> FEATURE:
<223> OTHER INFORMATION: oligonucleotide PCR primer

<400> SEQUENCE: 13
cgcggatcca tgcgcttgtg gaccccag                                   28
```